United States Patent
Kall

(10) Patent No.: US 10,211,650 B2
(45) Date of Patent: Feb. 19, 2019

(54) SYSTEM AND METHOD FOR MANAGING RECHARGABLE BATTERIES FOR MEDICAL DEVICES

(71) Applicant: General Electric Company, Schenectady, NY (US)

(72) Inventor: Magnus Kall, Helsinki (FI)

(73) Assignee: General Electric Company, Schenectady, NY (US)

(*) Notice: Subject to any disclaimer, the term of this patent is extended or adjusted under 35 U.S.C. 154(b) by 119 days.

(21) Appl. No.: 15/364,768

(22) Filed: Nov. 30, 2016

(65) Prior Publication Data

US 2018/0152029 A1    May 31, 2018

(51) Int. Cl.
   *H02J 7/00*      (2006.01)
   *G01R 31/36*     (2006.01)

(52) U.S. Cl.
   CPC ........ *H02J 7/0021* (2013.01); *G01R 31/3606* (2013.01); *G01R 31/3689* (2013.01); *A61B 2560/0214* (2013.01)

(58) Field of Classification Search
   CPC .................................................. H02J 7/0021
   USPC ......................................................... 320/107
   See application file for complete search history.

(56) References Cited

U.S. PATENT DOCUMENTS

| | | | |
|---|---|---|---|
| 5,594,345 A | 1/1997 | Boehm | |
| 9,440,550 B2* | 9/2016 | Jones | B60L 11/184 |
| 9,531,037 B2* | 12/2016 | Ogg | H01M 10/441 |
| 2003/0114899 A1* | 6/2003 | Woods | A61N 1/36071 607/60 |
| 2007/0210747 A1* | 9/2007 | Brandon, II | H02J 7/0003 320/114 |
| 2009/0021898 A1 | 1/2009 | Konno et al. | |
| 2013/0049762 A1* | 2/2013 | Ogg | H01M 10/4207 324/433 |
| 2013/0296669 A1* | 11/2013 | Chen | A61B 5/024 600/324 |
| 2014/0077815 A1* | 3/2014 | Mattisson | G01R 31/361 324/426 |
| 2014/0232340 A1* | 8/2014 | Jones | H02J 7/0027 320/109 |
| 2014/0275874 A1* | 9/2014 | Haisley | H02J 7/0042 600/323 |
| 2015/0023204 A1 | 1/2015 | Wik et al. | |
| 2016/0276858 A1* | 9/2016 | Davis | B60L 11/1861 |

* cited by examiner

*Primary Examiner* — Suchin Parihar
(74) *Attorney, Agent, or Firm* — Andrus Intellectual Property Law, LLP

(57) ABSTRACT

A system for managing rechargeable batteries for medical devices includes a charging station that holds and charges multiple batteries simultaneously and an idle time module that determines a battery idle time for one or more of the multiple batteries held in the charging stations, wherein the battery idle time indicates the duration that each respective battery has been fully charged and available for use. The system further includes a battery selection indicator for each of the multiple batteries, wherein the battery selection indicator is activated based on the battery idle time to identify that the respective battery should be selected for use.

20 Claims, 6 Drawing Sheets

| Batt ID | Station ID | Connect time | Connect charge level | Disconnect time | Disconnect charge level | Idle time | Average Idle time | Conditioning status | Min temp | Max temp | Actual Capacity | Design Capacity | Batt. optimization value | Device ID | Device connect time |
|---|---|---|---|---|---|---|---|---|---|---|---|---|---|---|---|
| | | | | | | | | | | | | | | | |

FIG. 5

SYSTEM AND METHOD FOR MANAGING RECHARGABLE BATTERIES FOR MEDICAL DEVICES

BACKGROUND

The present disclosure relates generally to battery management systems and methods, and more specifically to battery management systems and methods for managing a fleet of batteries for wireless patient monitoring devices.

Battery powered patient monitoring devices are becoming more common in the field of wireless patient monitoring and healthcare in general. Where multiple patient monitoring devices are being operated and maintained, large fleets of batteries must be constantly recharged and managed. Accordingly, charging stations have been developed that charge multiple batteries at once, which may range anywhere from a two battery charging station to a ten battery charging station, or more. Moreover, multiple charging stations may be operated throughout a medical facility to present convenient battery charging.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a system for managing rechargeable batteries for medical devices includes a charging station that holds and charges multiple batteries simultaneously and an idle time module that determines a battery idle time for one or more of the multiple batteries held in the charging station, wherein the battery idle time indicates the duration that each respective battery has been fully charged and available for use. The system further includes a battery selection indicator for each of the multiple batteries, wherein the battery selection indicator is activated based on the battery idle time to identify that the respective battery should be selected for use.

A method of managing rechargeable batteries for medical devices includes receiving multiple batteries in a charging station, charging each of the multiple batteries, and determining a charge completion time for each of the multiple batteries. The method further includes determining a battery idle time for each of the multiple batteries held in the charging station, wherein the battery idle time is based on the duration since the charge completion time. A battery selection indicator is then controlled for each of the multiple batteries based on the battery idle time for the respective battery, wherein the battery selection indicator is activated to identify that the respective battery should be selected for use.

Various other features, objects, and advantages of the invention will be made apparent from the following description taken together with the drawings.

BRIEF DESCRIPTION OF THE DRAWINGS

The present disclosure is described with reference to the following Figures.

FIG. 5 represents one embodiment of a battery profile in a battery management database.

DETAILED DESCRIPTION

Through his experience, experimentation, and research in the field of batteries for medical monitoring devices, the present inventor has recognized that a need exists for a battery management of rechargeable batteries for medical devices. For example, the present inventor has recognized that currently available battery charging systems and methods do not include battery optimization capabilities. For example, currently available charging systems and methods do not track indices of battery degradation or of situations that cause battery degradation to provide guidance to optimize battery utilization. For example, in a charging station that charges multiple batteries, certain batteries are selected less often than other batteries in the fleet, and some batteries sit idle in the charger for long periods of time. This can cause battery capacity to drop prematurely because battery chemistries deteriorate if they are not being used.

Accordingly, the inventor has recognized that a system for optimizing battery management should track factors that affect performance, such as number of charge discharge cycles, the amount of time that fully charged batteries sit idle in the charging station, and others. Furthermore, the inventor has recognized that a system is needed to indicate to users which batteries should be selected in order to optimize longevity of a fleet of batteries. Furthermore, the inventor has recognized that other indicators may be used, in addition to battery idle time, to monitor the battery fleet and optimize battery life over an entire fleet. For example, a battery optimization value may be calculated for each battery and/or group of batteries based on a battery charge level, capacity, conditioning status, temperature, and/or other battery statistics, such as usage time.

Figure 1:
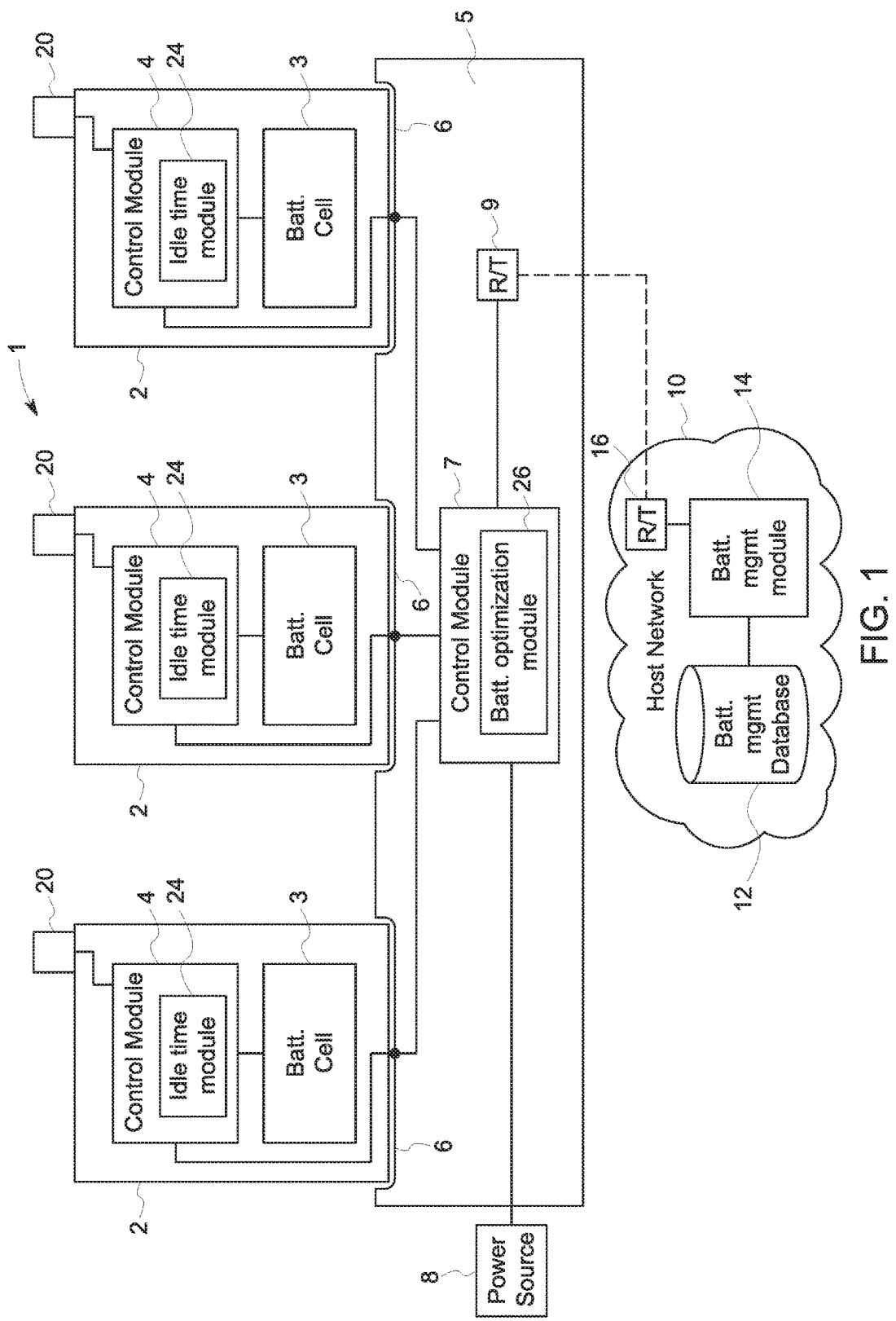
FIG. 1 is a block diagram of one embodiment of a system for managing rechargeable batteries for medical devices.

FIG. 1 depicts one embodiment of a system 1 for managing rechargeable batteries 2 for medical devices, such as wireless patient monitors. The system includes a charging station 5 that holds and charges multiple batteries 2 simultaneously. The charging station 5 receives power from a power source 8, such as by being plugged into a wall outlet at a medical facility. The charging station 5 has multiple battery holding locations 6 that receive any of various batteries 2 in the battery fleet and charge the battery 2. In the depicted embodiment, the charging station 5 has a control module 7 that controls distribution of the power from the power source 8 to the battery holding locations 6, and thus to the batteries 2 connected thereto. The control module 7 may also receive information about a respective battery 2 held in a battery holding location 6.

Additionally, each battery 2 may also contain a control module 4 that communicates information to the control module 7 of the charging station 5. For example, the control module 4 in the battery 2 may track the charge level of the one or more battery cell(s) 3 of the respective battery. Additionally, the control module 4 may track any number of battery performance factors. For example, the control module 4 may contain an idle time module 24, which may be a set of software instructions executable to determine a battery idle time for the respective battery 2, wherein the battery idle time indicates the duration that the respective battery has been fully charged and available for use. For example, the idle time module may contain a clock or counter that starts counting once the battery cell(s) 3 is completely charged and continues counting so long as the battery remains available for use. Battery availability may account for any number of factors. For example, a battery may be deemed "not available" if it is in need of conditioning or is currently undergoing a conditioning process. A fully charged battery may also be deemed not available if, for example, its internal temperature is in a suboptimal range, such as below a threshold low temperature or above a threshold high temperature.

The system 1 also includes a battery selection indicator 20 for each of the multiple batteries 2. The battery selection indicator 20 is activated based on the battery idle time for the respective battery 2. Namely, the battery selection indicator 20 is activated to identify that the respective battery should be selected for use. The battery selection indicator 20 may be located on each battery 2, or may be located on the charging station 5. The selection indicator 20 may take any of various forms, as described herein, which may provide a single visual indication of whether a battery should be selected (e.g., an "on/off" indicator) or may provide multiple levels of indication depending on the respective battery optimization value.

Figure 2:
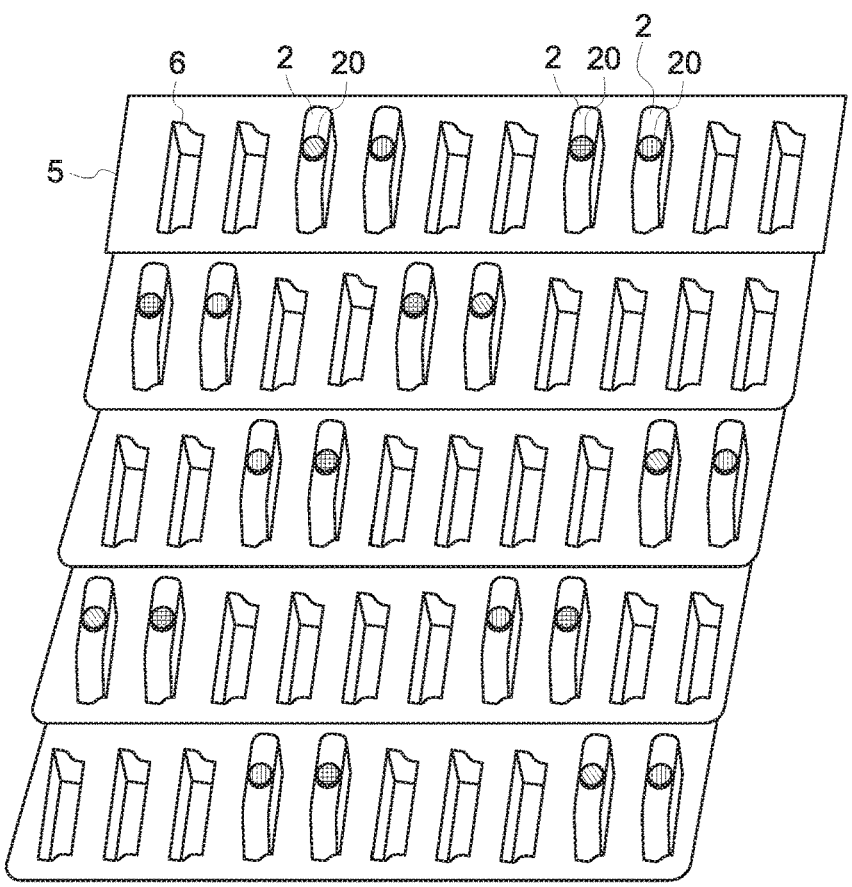
FIG. 2 depicts one embodiment of a charging station charging multiple batteries for medical devices.
Figure 3:
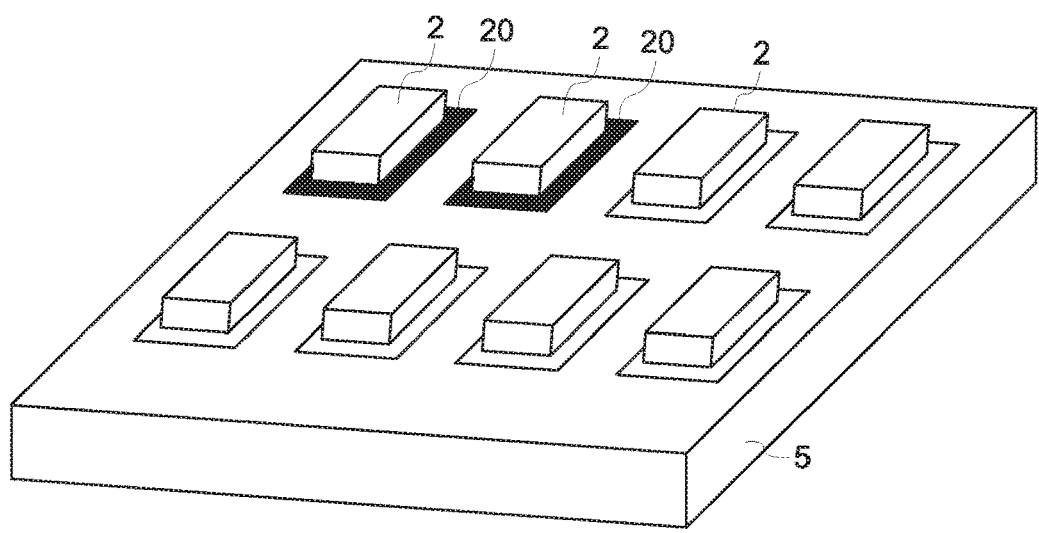
FIG. 3 depicts another embodiment of a charging station charging multiple batteries.

FIGS. 2 and 3 depict exemplary embodiments of battery charging stations 5 holding multiple batteries 2 in battery holding locations 6. In FIG. 2, each battery 2 has a battery selection indicator 20 that is a battery selection light that variously illuminates in different colors based on at least the battery idle time for the respective battery 2. In the depicted embodiment, the battery selection lights 20 illuminate in green to indicate that the battery should be selected for use. Batteries that are available for use, but have otherwise a lower priority have a battery selection light that is illuminated in yellow, while batteries that are not available have battery selection lights illuminated in red. Various illumination codes may be implemented in other embodiments, which may also include varying the intensity of the light and/or blinking the light for those batteries that are most optimal to be used.

FIG. 3 depicts another embodiment of a charging station 5 having multiple batteries 2 held therein and being charged. In the depicted embodiment, the battery selection indicator 20 is provided on the charging station 5 surrounding each battery 2 in its holding location 6. The battery selection indicators 20 in this embodiment are also battery selection lights, which are illuminable to indicate that the respective battery 2 should be selected for use. In the embodiment of FIG. 3, the battery selection indicator is only illuminated for those batteries which are suggested for selection by the user—e.g., those batteries 2 that are available for use and have the longest idle times of the batteries being held in the charger 5. In another example, the battery selection indicators 20 may be illuminated for those batteries 2 that are available for use and have an idle time above, or longer than, a threshold idle time. In still other embodiments, the battery selection indicator may be controlled in whole or in part based on an average idle time for the battery. For example, the average idle time for the battery may be accounted for in comparing the idle times of the batteries 2 being held in the charging station 5. For example, batteries 2 having high average idle times may be weighted for heavily in the analysis. Likewise, in an embodiment where the battery selection indicator 20 is controlled based on a threshold idle time, the threshold idle time could be decreased based on the battery's average idle time. In these ways, battery idle time can be managed and/or equalized across a fleet of batteries.

The battery selection indicator 20 may be an illuminable element, such as a variously illuminable battery selection light as described above, or it may be any other element capable of visually displaying or indicating to a user which battery should be selected. For example, the battery selection indicator 20 could be a grid on the charging station 5 that indicates which battery should be selected. In another embodiment, the battery selection indicator could include physically moving or positioning each battery 2 in a way that can indicate to the user which battery should be selected. For example, batteries 2 that are indicated for selection could be elevated or the visual indicator could comprise a cover or lock over the battery that is opened to indicate that the battery should be selected for use and allows the respective battery 2 to be removed from the charging station 5.

The system 1 may include a battery optimization module 26 that receives information about one or more performance indicators, or factors, and controls the battery selection indicator 20 accordingly. In such an embodiment, the battery optimization module 26 may be contained within the control module 4 of each battery 2, or it may be contained in the control module 7 of the charging station 5. Additionally, the battery optimization module 26 may be configured to perform comparative analysis between the performance indicators for the various batteries 2 being held in the charging station 5. In such embodiments, the battery optimization module 26 may be located in the control module 7 of the charging station 5, which may receive information regarding the performance indicators from each control module 4 in each battery 2 held in the charging station 5. In still other embodiments, the battery selection indicator 20 may be controlled based only on battery idle time, rather than based on a battery optimization value determined by analysis of additional performance indicators. In such an embodiment, the system 1 may not include any battery optimization module, and the battery selection indicator 20 may be controlled by the idle time module 24 and/or the control module 4 of the battery 2.

In the depicted embodiment, each battery 2 being held in the charging station 5 has an idle time module 24 in or associated with the local control module 4. However, in other embodiments the charging station 5 may include a centralized idle time module 24 in the control module 27 that receives information from the control module 4 of each battery, and the centralized idle time module 24 would then calculate an idle time for each battery 2 being held in the charging station 5. In such an embodiment where the control module 7 controls activation of the battery selection indicator 20, the control module 7 may communicate directly with the battery selection indicator 20 (such as if the battery selection indicator 20 is housed on the charging station 5), or the control module 7 of the charging station 5 may communicate control commands to the control module 4 of each battery 2, which would then activate the battery selection indicator 20 accordingly.

Figure 4:
FIG. 4 represents one embodiment of a table for calculating a battery optimization value.

In certain embodiments, the battery optimization module 26 may execute an algorithm that determines activation of the battery selection indicator 20. As described above, the battery optimization module 26 may consider multiple factors in addition to battery idle time, and may also account for a comparison of the performance indicators in the multiple batteries 2 being held in the charging station 5. FIG. 4 represents one embodiment of an algorithm that could be executed by the battery optimization module 26 and used as a basis of control for the battery selection indicator 20. The table in FIG. 4 presents various control instructions based on temperature 31, idle time 32, conditioning status 33, capacity 34, and charge level 35. For each performance indicator 31-35, multiple optimization calculation values 40 may be assigned based on the value of the respective performance indicator 31-35. In one embodiment, the optimization calculation values 40 for each of the performance indicators 31-35 are then added to determine the battery optimization value. However, certain performance indicators yield an assignment of "not available" to the battery. In one embodiment, a battery may be deemed to not be available for use if any of the performance indicators 31-35 have optimization calculation values 40 indicating "not available".

As depicted in the table of FIG. 4, different weights, or optimization calculation values 40, may be assigned to different performance indicators. For example, the depicted embodiment is configured such that idle time, and specifically idle time values trending towards the longer end of the spectrum, receive the heaviest weight in determining the battery optimization value. Charge level 35 receives the second most weight when the battery 2 is fully charged.

In the depicted embodiment, the temperature 31 is divided into five ranges between 10° Celsius and 41° Celsius. If the battery is below 10° Celsius or above 41° Celsius then it is assigned "not available" status. The range between the low temperature threshold and the high temperature threshold is subdivided into three ranges, where batteries within the optimal range receive an optimization calculation value 40 of one, and the temperatures outside the optimal range but within the thresholds are assigned an optimization calculation value of zero. For idle time 32, which as described above is the amount of time that the respective battery is held in the charging station while fully charged and available for use, is divided into five ranges. The first range is immediately upon reaching full charge. In the depicted embodiment, the optimization calculation values 40 for idle time 32 make the battery available immediately upon reaching full charge. Increasing optimization calculation values 40 are assigned as the idle time 32 increases, with the highest value assigned for those batteries with long battery idle times, such as battery idle times that are longer than a threshold idle time.

The table also provides optimization calculation values 40 for the conditioning status 33 of each battery 2. The conditioning status indicates whether a battery has recently been conditioned or is in need of conditioning. The conditioning status 33 may also provide a "not available" indicator when the battery is going through the conditioning process. Battery conditioning is a process whereby the battery life measurement is recalibrated. Battery life calculations are generally estimates based on total charge capacity and usage amount since the last charge. Battery capacity decreases over many charge/discharge cycles. At some point the estimate providing the basis of the battery life calculation is no longer accurate because the charge capacity has decreased. Thus, the battery life is remeasured in a conditioning process that involves charging the battery cell(s) 3 in the battery 2 to a full charge and then completely discharging the battery cell(s) 3. The amount of energy output from the battery between full charge and complete discharge is measured, which then forms the updated and more accurate estimate upon which the battery life monitoring will be based. In the table of FIG. 4, optimization calculation values 40 of one are assigned to recently conditioned batteries, and a value of zero is then assigned after multiple charge/discharge cycles until such time as the battery is determined to need conditioning. For example, the determination may be based on number of charge/discharge cycles if the battery is determined to need conditioning, then it is assigned "not available" status.

As described above, battery capacity decreases over the life of a battery, which may be due to charge/discharge cycles and the length of time that the battery sits idle (either on the charger or off the charger but not being used) between charge/discharge cycles. The capacity value 34 provides an indicator of where in its lifespan the battery is. For example, the capacity 34 performance indicator may be expressed as a ratio of current capacity to design capacity (the charge amount that the battery provided at the beginning of its life and/or the amount of power that the battery was intended to provide). In the table of FIG. 4, optimization calculation values 40 are provided for batteries between 75% and 100% capacity, where the optimization calculation values 40 decrease as the capacity 34 decreases. Finally, charge level 35 is another performance indicator used to determine the battery optimization value. In the depicted embodiment, a battery 2 is deemed "not available" until it approaches 100% charge level, which in the depicted embodiment is assigned an optimization calculation value 40 of two. Alternatively or additionally, other performance indication parameters may be utilized. To provide an additional example, in a battery 2 containing multiple cells 3, cell balance—i.e. how well the cell(s) 3 within the battery back are equally charged, or balanced—could be utilized as another performance indicator value accounted for in determining the battery optimization value.

The optimization calculation values 40 determined based on the performance indicators 31-35 are then added together and, assuming that none of the performance indicators yield a "not available" status, the battery optimization value is determined as the sum of the optimization calculation values 40. The battery selection indicator 20 can then be controlled based on the battery optimization value. For example, the battery selection indicator may be illuminated for batteries 2 with battery optimization values above a threshold value. Additionally, as described above, the battery selection indicator may be variously controlled based on the battery optimization value. For example, the battery selection indicator may get brighter, blink, or otherwise indicate those batteries with the highest battery optimization value. To that end, the battery optimization module 26 may compare the battery optimization values for each battery 2 held in the charging station 5, and may indicate a high priority for the one or more batteries held in the charger having the longest battery idle time. In certain examples, the high priority indication may be altering the battery selection indicator 20, such as to make it brighter, change its color, blink, etc.

In certain embodiments, the system 1 for managing rechargeable batteries 2 may include multiple charging stations 5 networked to a host network 10. The host network 10 may include a battery management module 14 that receives information transmitted by each charging station 5 and stores that information in a battery management database 12. Each charging station 5 may transmit battery profile data for each battery 2 held in the charging station to the host network 10, which may be by any wired or wireless means. In the depicted example, the charging station 5 has a wireless receiver transmitter 9 in wireless communication with a receiver transmitter 16 in the host network 10. The respective receiver transmitter 9, 16 may communicate according to any of various wireless protocols, such as operating on the wireless medical telemetry service (WMTS) spectrum or on a Wi-Fi compliant wireless local area network (WLAN). In still other embodiments, wireless communication may be provided via Bluetooth, Bluetooth low energy, ANT, Zig-Bee, or the like.

The battery management database 12 in the host network 10 may be a database of battery profiles for every battery 2 in the fleet of batteries that connects to a charging station 5 within the system 1. An exemplary battery profile is depicted in FIG. 5, which is keyed off of the battery identification number (battery ID) for each battery 2 within the system 1. The battery profile also includes, or stores, a station identification number (station ID) for each charging station 5 that the battery has connected to, along with a connection time at which the respective battery 2 connected to the charging station 5 and a charge level of the battery cell(s) 3 in the battery 2 at the time of connection with that charging station 5. The exemplary battery profile also includes a disconnect time, which is the time that the battery 2 was removed from the charging station 5, along with a disconnect charge level. An idle time is also provided, which is the amount of time that the battery 2 was on the charging station 5 while fully charged and available for use. The battery profile may also include an average idle time, which is a running average of all the idle times experienced by the respective battery 2. The battery profile also includes a conditioning status, which may be the conditioning status at the time that the battery 2 is disconnected from the charging station. The depicted battery profile also includes a minimum temperature and maximum temperature experienced by the battery while connected to the respective charging station 5. The battery profile may also include information about the capacity of the respective battery 2, such as the actual capacity of the battery at each charging cycle and the design capacity of the battery 2 (e.g. which could be utilized to determine the capacity performance indicator 34. The profile might also include the battery optimization value, such as the battery optimization value at the time that the battery was disconnected from the charging station. Moreover, additionally, the battery profile may also provide battery tracking information, such as a device identification number for each medical device, such as each wireless patient monitor, that the respective battery 2 connects to. Additional information for purposes of battery tracking may include the time that the battery 2 was connected and/or disconnected from the medical device.

The battery profile information may be utilized by the battery management module 14 in the host network 10 to provide relevant information for monitoring and optimizing a fleet of batteries. For example, the battery management module 14 may track the battery profiles and identify certain areas, such as certain regions of a medical facility, where battery idle times are especially high. In that instance, the batteries in the low usage area where idle times are high may be swapped with batteries in a high usage area with very low average idle times. Alternatively or additionally, such information may be used to determine how many batteries to maintain in each area of the medical facility. For example, the battery profile data may indicate that batteries are being taken from the charger before being fully charged, which may indicate an insufficient number of batteries are available in a particular area. Such information can be used to ensure that the correct number of batteries are being provided based on information gleaned from the battery profiles.

Figure 6:
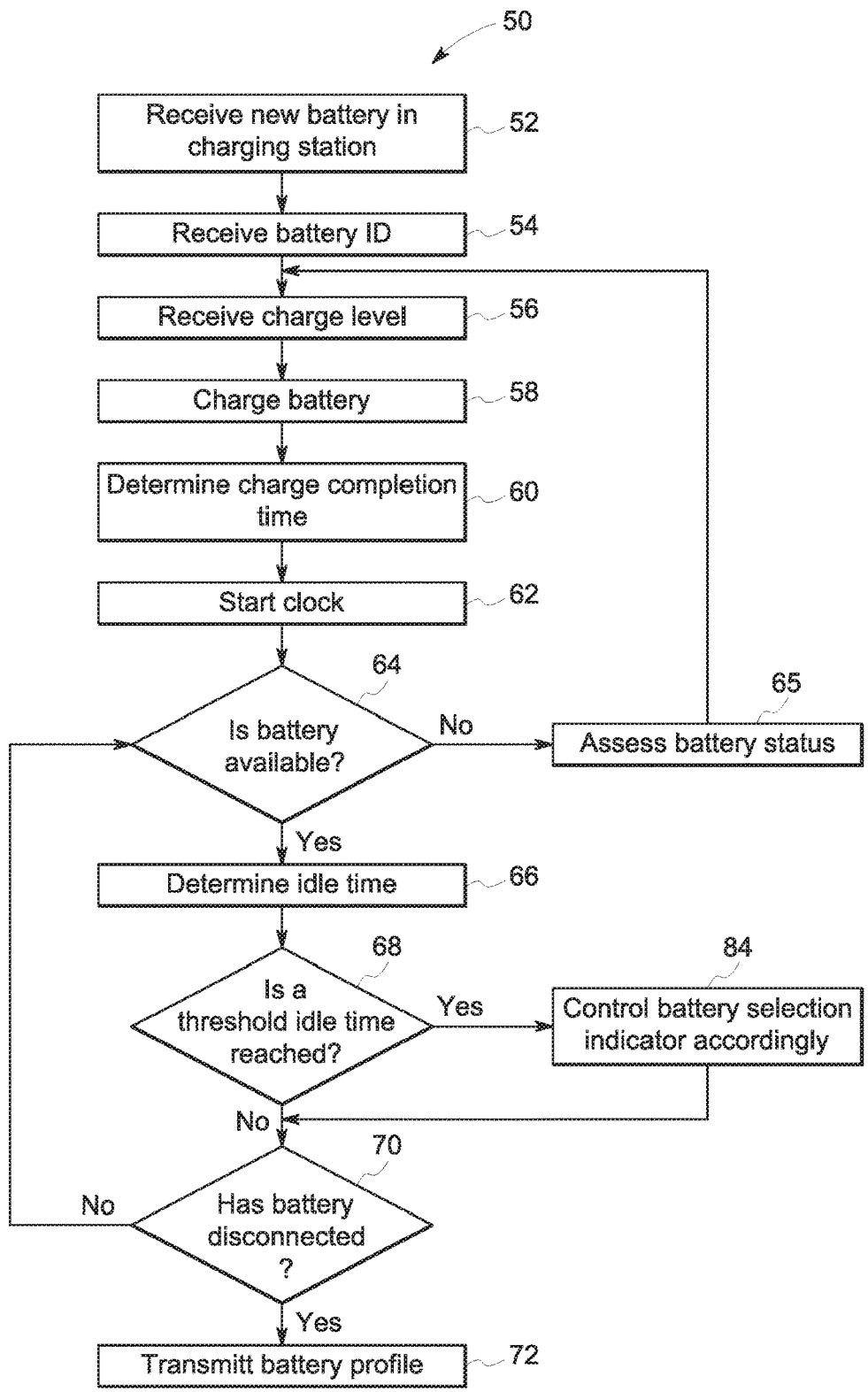
FIG. 6 depicts one embodiment of a method for managing rechargeable batteries of medical devices.
Figure 7:
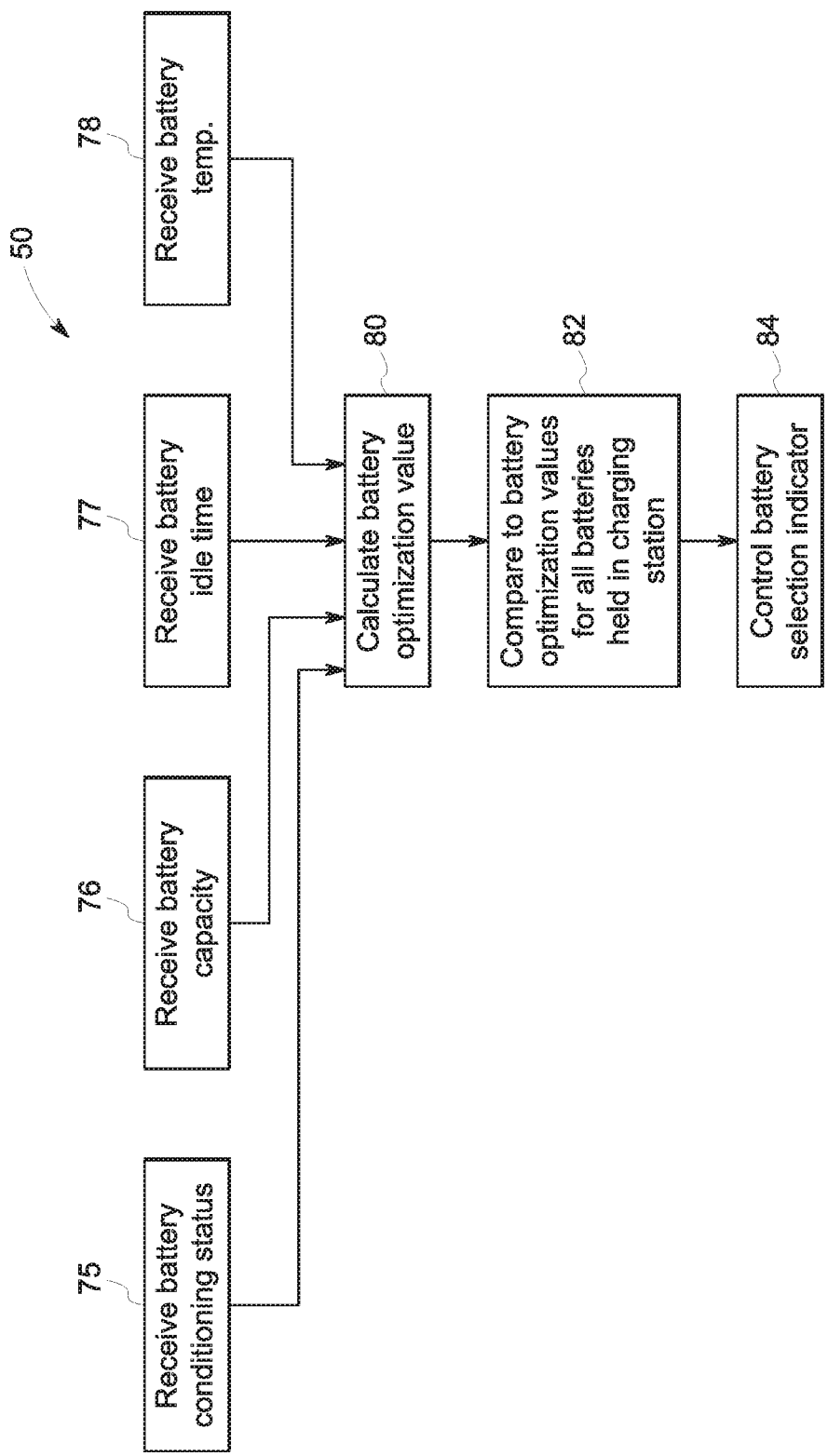
FIG. 7 depicts another embodiment of a method for managing rechargeable batteries for medical devices.

FIGS. 6 and 7 depict embodiments of a method 50 of managing rechargeable batteries for medical devices. A new battery 2 is received at the charging station 5 at step 52. A battery ID is received at step 54, such as received at the control module 7 within the charging station 5 from the control module 4 in the battery 2. The control module 7 also receives a charge level at step 56, which is the charge level of the battery cell(s) 3 within the battery 2 at the time of connecting to the charging station 5. The charging station 5 then charges the battery 2 at step 58. Instructions are executed at step 60 to determine a charge completion time, which is the time that the battery cell(s) 3 reaches full charge. A clock or timer is started at step 62 to begin counting battery idle time. Step 64 determines whether the battery 2 is available for use, such as whether any of the performance indicators have an optimization calculation value 40 of "not available" as shown in FIG. 4. An idle time is determined at step 66 based on the clock, or timer, value. Steps are executed at steps 68 to determine whether the idle time has reached a threshold idle time, such as a threshold in the table of FIG. 4 upon which a new optimization calculation value 40 would be assigned. Alternatively, the threshold idle time may be a different threshold upon which the battery selection indicator would be controlled. The battery selection indicator 20 is controlled accordingly at step 84, such as according to the method exemplified in FIG. 7. Step 70 is executed to determine whether the battery 2 has been disconnected from the charging station 5. If not then the method returns to step 64 to verify that the battery 2 remains available. If the battery 2 is assigned a "not available" status, then step 65 is executed to assess the battery status, such as to begin a conditioning cycle or to take steps to reduce the battery temperature. Depending on the cause of the battery unavailability, different steps may be executed. In the depicted embodiment, the method returns to step 56 to determine whether the battery cell(s) 3 of the respective battery 2 is fully charged. Returning to step 70, if the battery is disconnected from the charging station 5, the control module 7 transmits the battery profile to the host network 10 for storage in the battery management database. For example, the steps depicted at FIG. 6 could be executed by an idle time module 24, which could be associated with the control module 4 in the battery 2 or the control module 7 in the charging station 5, as is described above.

FIG. 7 depicts another embodiment of a method 50 of managing rechargeable batteries for medical devices. For example, the method steps depicted in FIG. 7 could be executed by a battery optimization module 26 in a control module 7 of the charging station 5. A battery conditioning status is received at step 75 and a battery capacity is received at step 76, such as from a control module 4 in each respective battery 2. A battery idle time 32 is received at step 77, such as from a battery idle time module 24. The battery temperature is received at step 78, such as from the battery control module 4 in the battery 2 or directly from a temperature sensor in the battery 2. A battery optimization value is calculated at step 80 based on the received performance indicators, one example of which is described above with respect to FIG. 4. In the depicted embodiment, further steps are executed to compare the battery optimization values for all batteries held in the charging station to determine which batteries have the highest optimization values, and thus which ones should receive a priority designation to indicate to a user that such batteries should be selected. The battery selection indicator is controlled accordingly at step 84.

Aspects of the disclosure are described herein in terms of functional and/or logical block components and various processing steps. It should be appreciated that such block components, including the "modules" described herein, may be realized by any number of hardware, software, and/or firmware components configured to perform the specified functions. For example, an embodiment may employ various integrated circuit components, e.g., memory elements, digital signal processing elements, logic elements, look-up tables, or the like, which may carry out a variety of functions under the control of one or more processors or other control devices. As used herein, the term module may refer to software code, and also may include an application-specific integrated circuit (ASIC), an electronic circuit, a combinational logic circuit, a field programmable gate array (FPGA), a processor (shared, dedicated, or group) that executes the code, or other suitable components that provide the described functionality, or a combination of some or all of the above, such as in a system-on-chip. The term module may also include memory (shared, dedicated, or group) that stores code executed by the processor. The term code, as used herein, may include software, firmware, and/or microcode, and may refer to programs, routines, functions, classes, and/or objects. The term shared, as used above, means that some or all code from multiple modules may be executed using a single (shared) processor. In addition, some or all code to be executed by multiple different processors may be stored by a single (shared) memory. The term group, as used above, means that some or all code comprising part of a single module may be executed using a group of processors. Likewise, some or all code comprising a single module may be stored using a group of memories.

FIG. 1 provides a system diagram of one exemplary embodiment of a system 1 for managing batteries having an idle time module 24 and a battery optimization module 26, which in the depicted embodiment may be software applications within the control modules 4,7. Namely, each of the modules 24 and 26 include computer-readable instructions that, when executed on a processor in one of the control modules 4,7, direct operation as described in further detail herein.

Although the system 1 depicted in FIG. 1 includes a control module 4 in each battery 2 and a separate control module 7 in the charging station 5, it should be understood that a single control module may provide the same operation, such as a single control module 7 in the charging station 5. Likewise, the system may be configure with no control module in the charging station 5, and all of the control functions for controlling the battery selection indicator may be performed by control modules 4 contained in each battery 2. Likewise, it should be understood that the some or all of the functions described herein as performed by the idle time module 24 and a battery optimization module 26 may be combined and performed by a single software application—i.e., some or all of the instructions described as being part of the idle time module 24 and a battery optimization module 26 may be provided in a single set of software instructions called and executed on a processor in any of the battery 2, the charging station 5, and/or the host network 10.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A system for managing rechargeable batteries for medical devices, the system comprising:
   a charging station that holds and charges multiple batteries simultaneously;
   an idle time module that determines a battery idle time for one or more of the multiple batteries held in the charging station, wherein the battery idle time indicates the duration that each respective battery has been fully charged and available for use; and
   a battery selection indicator for each of the multiple batteries, wherein the battery selection indicator is activated based on the battery idle time to identify that the respective battery should be selected for use.

2. The system of claim 1, further comprising a battery optimization module that: calculates a battery optimization value based on the battery idle time and one or more of a battery conditioning status, a battery charge level, a battery capacity, a battery temperature; and controls activation of the battery selection indicator based on the battery optimization value.

3. The system of claim 2, wherein each of the multiple batteries held in the charging station is associated with one battery selection indicator in the form of a battery selection light that variously illuminates based on the battery optimization value for the respective battery.

4. The system of claim 2, wherein each of the multiple batteries held in the charging station contains one idle time module and one battery optimization module.

5. The system of claim 2, wherein the charging station contains one battery selection indicator for each battery holding location, and wherein the battery selection indicator is controllable based on the battery optimization value for the battery in the holding location.

6. The system of claim 2, wherein the battery optimization module is contained in the charging station and receives the battery idle time from the idle time module in each of one or more of the batteries held in the charging station; and
   wherein the battery optimization module activates the battery selection indicator for each battery for which the battery idle time is longer than a threshold idle time.

7. The system of claim 6, wherein the battery optimization module compares the battery idle times of the batteries held in the charging station and controls the battery selection indicator to indicate a high priority for one or more of the batteries held in the charger having a longest battery idle time.

8. The system of claim 1, wherein the idle time module receives a battery conditioning status indicating that the battery is being conditioned and determines that the respective battery is not available for use.

9. The system of claim 1, wherein the idle time module receives a battery temperature, and determines that the respective battery is not available for use if the battery temperature is above a threshold high temperature or below a threshold low temperature.

10. The system of claim 1, wherein the battery optimization module is contained in the charging station and receives the battery idle time from the idle time module in each of one or more of the batteries held in the charging station; and
   wherein the battery optimization module activates the battery selection indicator for each battery for which the battery idle time is longer than a threshold idle time; and wherein the battery optimization module compares the battery idle times of the batteries held in the charging station and controls the battery selection indicator to indicate a high priority for one or more of the batteries held in the charger having a longest battery idle time.

11. The system of claim 1, further comprising multiple charging stations, each having a station ID;
wherein each charging station is communicatively connected to a host network containing a battery management database;
wherein the battery management database stores a battery profile for each battery held by one of the multiple charging stations; and
wherein the battery profile contains battery idle times for the respective battery.

12. The system of claim 11, wherein each charging station updates the battery profile for each of the multiple batteries being held therein.

13. The system of claim 11, wherein each battery profile contains the station ID, a connection time, and a disconnection time for each charging station to which the respective battery has been held.

14. The system of claim 13, further comprising a battery management module in the host network, wherein the battery management module identifies batteries with an average idle time longer than a threshold average idle time.

15. A method of managing rechargeable batteries for medical devices, the method comprising:
receiving multiple batteries in a charging station;
charging each of the multiple batteries;
determining a charge completion time for each of the multiple batteries;
determining a battery idle time for each of the multiple batteries held in the charging station, wherein the battery idle time is based on the duration since the charge completion time; and
controlling a battery selection indicator for each of the multiple batteries based on the battery idle time for the respective battery, wherein the battery selection indicator is activated to identify that the respective battery should be selected for use.

16. The method of claim 15, wherein the battery selection indicator is a battery selection light that variously illuminates based on at least the battery idle time for the respective battery.

17. The method of claim 15, further comprising:
comparing the battery idle times of each of the batteries held in the charging station; and
controlling the battery selection indicator to indicate a high priority for one or more of the batteries held in the charger having a longest battery idle time.

18. The method of claim 15, further comprising:
calculating a battery optimization value based on the battery idle time and one or more of a battery conditioning status, a battery charge level, a battery capacity, a battery temperature; and
controlling the battery selection indicator based on the battery optimization value.

19. The method of claim 18, further comprising activating the battery selection indicator for each battery having a battery idle time longer than a threshold idle time.

20. The method of claim 18, further comprising:
comparing the battery optimization values of the batteries held in the charging station; and
controlling the battery selection indicator to indicate a high priority for one or more of the batteries held in the charger having a highest battery optimization value.

* * * * *